(12) United States Patent
DeMayo

(10) Patent No.: US 6,383,149 B1
(45) Date of Patent: May 7, 2002

(54) LASER LENGTH DISCREPANCY DEVICE

(75) Inventor: Edward DeMayo, Greenbrae, CA (US)

(73) Assignee: Innovative Medical Products, Plainville, CT (US)

( * ) Notice: Subject to any disclaimer, the term of this patent is extended or adjusted under 35 U.S.C. 154(b) by 0 days.

(21) Appl. No.: 09/679,622

(22) Filed: Oct. 5, 2000

(51) Int. Cl.[7] .......................... A61B 5/103; A61B 5/117
(52) U.S. Cl. ........................ 600/587; 606/102; 33/511
(58) Field of Search ................. 600/587, 595; 33/511, 512; 606/53, 102

(56) References Cited

U.S. PATENT DOCUMENTS

| | | | | |
|---|---|---|---|---|
| 5,249,581 A | * | 10/1993 | Horbal et al. | 600/407 |
| 5,482,283 A | * | 1/1996 | Wall | 473/220 |
| 5,606,590 A | * | 2/1997 | Petersen et al. | 378/177 |
| 5,864,956 A | * | 2/1999 | Dong | 33/227 |
| 5,989,245 A | * | 11/1999 | Prescott | 606/14 |
| 6,027,507 A | * | 2/2000 | Anderson et al. | 606/102 |
| 6,209,219 B1 | * | 4/2001 | Wakefield et al. | 33/761 |
| 6,214,014 B1 | * | 4/2001 | McGann | 606/102 |
| 6,230,416 B1 | * | 5/2001 | Trigilio | 33/474 |

* cited by examiner

Primary Examiner—Kevin Shaver
Assistant Examiner—Charles Marmor, II

(57) ABSTRACT

A simple hand-held length discrepancy device in the form of a pair of laser diodes separated a fixed distance within a console determines the length of a patient's leg after hip replacement surgery. A self-tapping first indication screw is partially inserted within the patient's pelvis prior to surgery, the first laser beam is directed on the screw and the second laser beam is directed on the patient's leg. The location of the second laser beam is recorded by means of a second indelible ink mark or a second drill hole. After surgery, the first and second laser beams are again directed on the first indication screw on the hip and the second mark or drill hole on the leg to determine any change in distance there between.

8 Claims, 3 Drawing Sheets

LASER LENGTH DISCREPANCY DEVICE

BACKGROUND OF THE INVENTION

It is difficult during joint replacement within the human body to maintain the exact overall leg dimension after surgery. This is especially true when large joints such as hips, are repaired and or completely replaced.

One method for comparing leg length before and after hip surgery is described within U.S. Pat. No. 6,027,507 entitled "Leg Length Gauge for Total Hip Replacement", wherein a removable gauge having pin-receiving apertures is employed.

U.S. Pat. No. 5,606,590 entitled "Surgical Laser Beam-based Alignment System and Method" describes a sophisticated x-ray console that includes a laser source and lens for providing alignment during orthopedic surgery.

A further use of a laser distance detector for manufacturing operations is found in U.S. Pat. No. 4,733,969 entitled "Laser Probe for Determining Distance." This arrangement employs lenses along with an electronic circuit, which functions as a coordinate measuring machine.

It would be economically advantageous to utilize the precision focus of inexpensive laser diodes, per se, without having to provide lenses and electronic circuits for distance determination during medical procedures.

One purpose of the instant invention is to provide a simple, non-invasive arrangement of laser diodes for determining pre-operative and post-operative limb and joint distance for maintaining or correcting the distance after surgical joint replacement.

SUMMARY OF THE INVENTION

A hand-held measurement console and surgical position indicator in the form of an enclosure containing a pair of spaced lasers is used in conjunction with a pair of temporary markers in the form of screws, indelible markings and the like, to determine a reference distance prior to joint replacement surgery. Immediately after surgery, the lasers are directed on the temporary markers to compare the post surgery distance to the reference distance and appropriate adjustments are made to cause the post-surgery distance to correspond to the pre-surgery reference distance or the desired leg length correction.

DESCRIPTION OF THE PREFERRED EMBODIMENT

SUMMARY OF THE INVENTION

A hand-held length discrepancy device and surgical position indicating in the form of a pair of laser diodes separated a fixed distance within a console determines the length of a patient's leg before and after hip replacement surgery. The device is aligned with the patient by means of a level incorporated therein. A self-tapping first indication screw is partially inserted in the pelvis above the patient's hip prior to surgery. The first laser beam is directed on the screw and the second laser beam is directed on the femoral trochanter. The location of the second laser beam is recorded by means of a second indelible ink mark, electrocantery mark or a second drill hole. After surgery, the first laser beam is again directed on the first indication screw in the pelvis and the second laser beam is compared to the mark on the trochanter to determine any change in distance there between.

Figure 1:
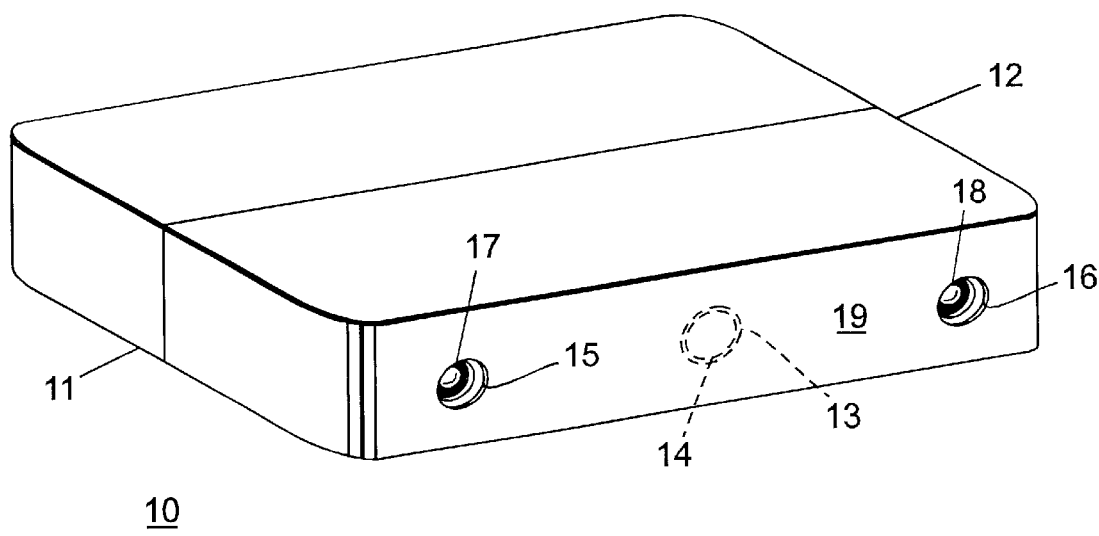
FIG. 1 is an enlarged top front perspective view of the length comparison device according to the invention.

The length comparison and surgical position indicator device 10, according to the invention, is shown in FIG. 1 to consist of a plastic case 11 to which a plastic cover 12 is removably attached. A top opening 13 is formed within the cover 12 for accessing the on-off push button switch 14.

A first opening 15 is formed within the front 19 of the cover 12 for providing transmission from a proximate laser diode 17 and a second opening 16 is formed therein for providing transmission from a distal laser diode 18. The proximate and distal lasers 17, 18 are class 3A low voltage 635 nanometer diodes turned on and off by means of the low voltage switch 14 in the manner to be described below.

Figure 2:
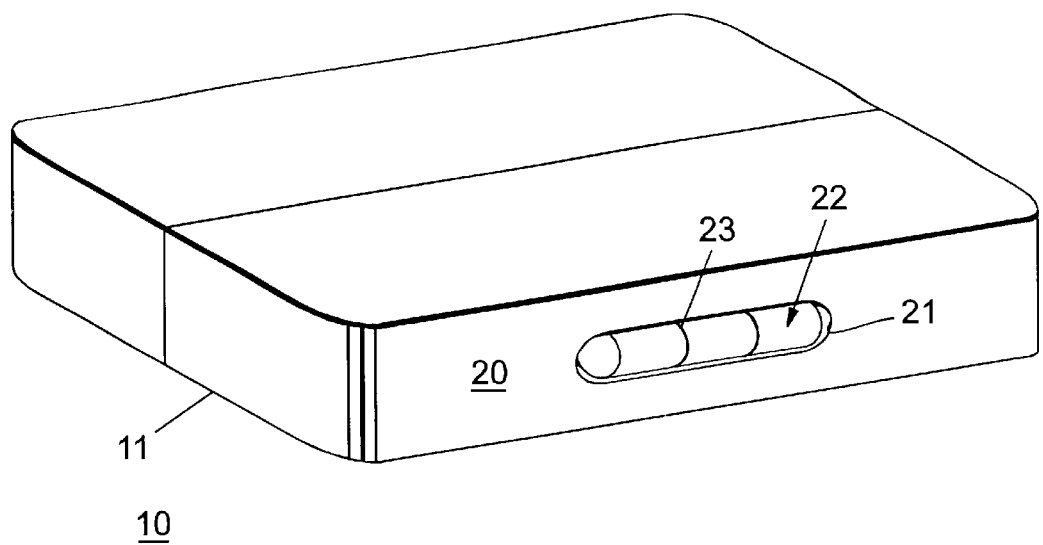
FIG. 2 is an enlarged top rear perspective view of the length comparison device of FIG. 1.

The rear 20 of the length comparison device 10 is shown in FIG. 2 to depict the level gauge 22 extending within the elongated aperture 21 formed within the rear 20 of the case 11. The level gauge is of the type that includes a pair of level lines 23 and a bubble (not shown) for insuring precision line-up of the proximate and distal laser diodes 17, 18 in the manner to be described below.

Figure 3:
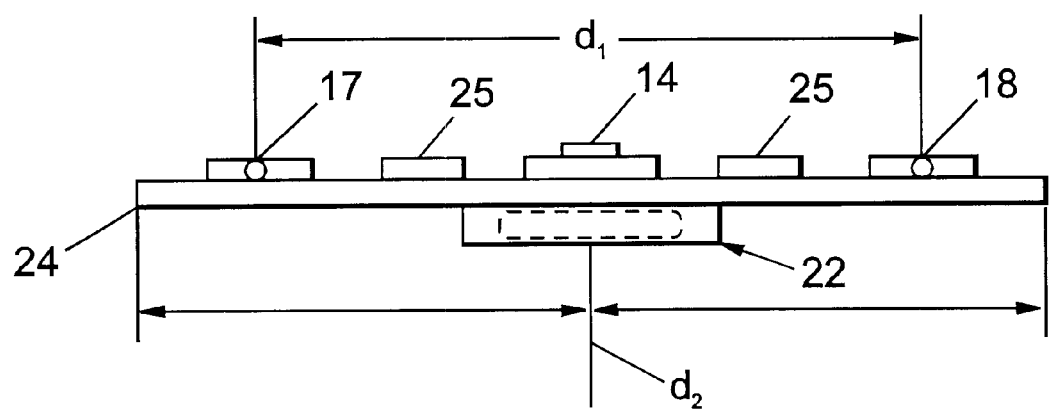
FIG. 3 is front view of the circuit board and components contained within the length comparison device of FIGS. 1 and 2.
Figure 4:
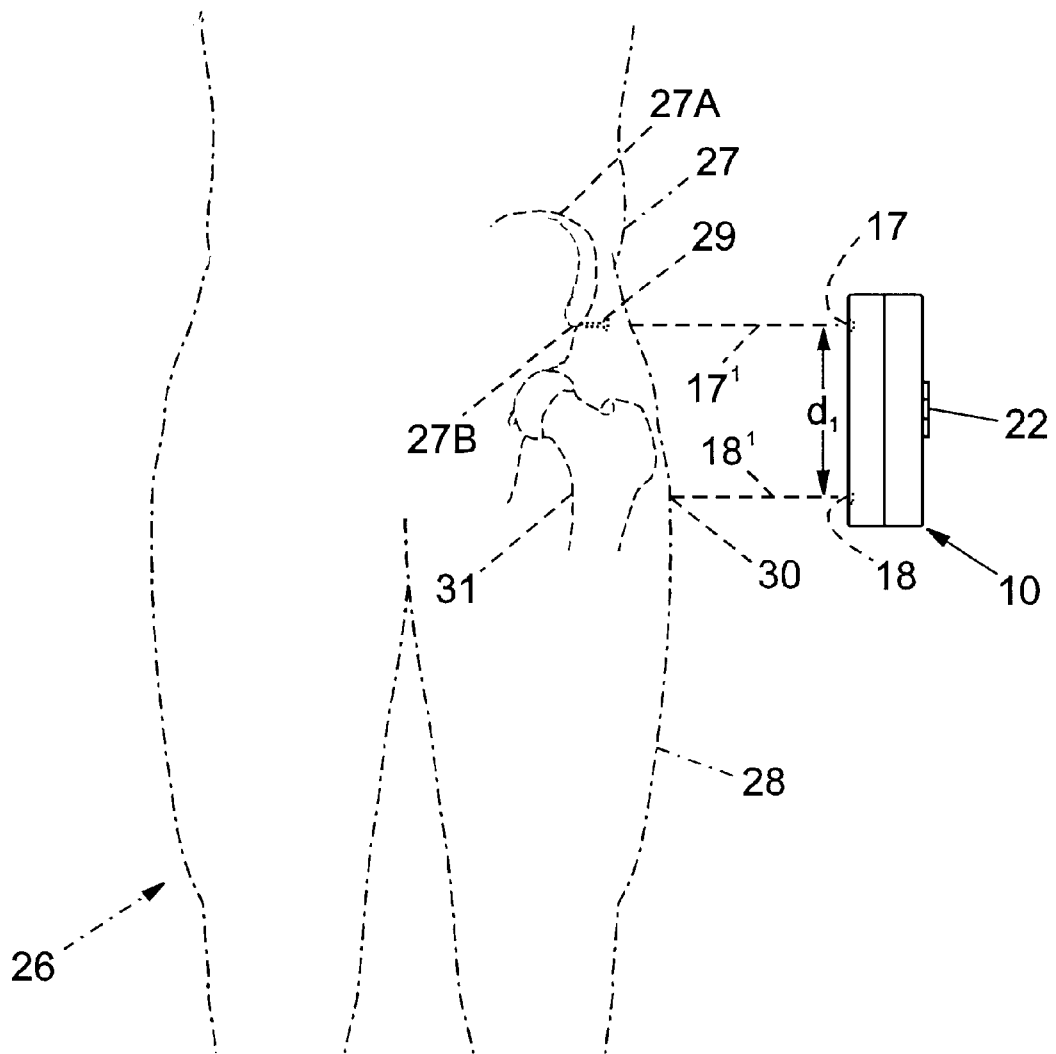
FIG. 4 is top perspective view of the length comparison device of FIGS. 1 and 2 relative to a person, as shown in phantom.

The arrangement of the proximate and distal lasers 17, 18 within the length comparison device 10 of FIG. 1 is best seen by now referring to the printed circuit board 24 shown in FIG. 3. The proximate and distal lasers 17, 18 are arranged a predetermined distance $d_1$ on the top of the printed circuit board 24 on opposite sides of the push button switch 14 and 1.5 volt dry cell miniature batteries as indicated at 25. The level gauge 22 is positioned on the bottom of the printed circuit board 24 at the center thereof as indicated at $d_2$. One use of the length comparison device 10 for determining the positioning of a hip 27 relative to a leg 28 of a patient 26 before and after hip replacement surgery is depicted in FIG. 4.

During the hip replacement surgery, the acetabulum 27A is exposed and a short self-tapping surgical-type screw 29 is inserted into the pelvis as indicated at 27B. It is noted that the screw 29 is out of the way during the hip replacement procedure and serves as a reproducible, non-moving target during the procedure. Before dislocating the hip 27, the patient's leg 28 is held in a level position and the length comparison device 10 is employed in the following manner. The length comparison device 10 is arranged proximate the hip 27 and leg 28, and the level gauge 22 is viewed for adjusting the length comparison device to a level position relative to the patient's leg and hip. The proximate laser 17' is focused on the screw 29 as indicated at 17' and a drill hole 30 is formed at the point of focus of the distal laser 18 at the predetermined distance $d_1$ on the patient's leg 28 over the greater trochanter 31, as indicated at 18'. Although a drill hole 30 is indicated, a colored dye could be used alternatively. Upon replacement of the hip 27, the procedure is repeated for comparing the positional relationship between the proximate and distal lasers 17', 18' via the screw 29, screw hole 30, and focus beams 17', 18'. The leg 28 is then shortened or lengthened to compensate for any change in relation the predetermined distance $d_1$.

Although the simple length comparison unit 10 is depicted for hip replacement surgery, it is understood that the same unit can be used with other types corrective and replacement surgery to correct for post-operative distance changes.

What is claimed is:

1. A hand-held surgical position indicator comprising:

a cover and a case joined together to form an enclosure;

a pair of first and second apertures in said enclosure, having a fixed separation distance there between;

a circuit board within said enclosure;

a first laser diode mounted on said circuit board, said first laser diode arranged proximate said first aperture for projecting a first light beam through said first aperture;

a second laser diode mounted on said circuit board, said second laser diode arranged proximate said second aperture for projecting a second light beam through said second aperture, said first and second light beams being separated said fixed separation distance;

switch means on said enclosure connecting with said first and second laser diodes for simultaneous excitation; and power means on said printed circuit board for providing operating power to said first and second laser diodes.

2. The position indicator of claim 1 wherein said switch comprises a push button switch.

3. The position indicator of claim 1 wherein said power means comprises a power supply or a battery.

4. The position indicator of claim 1 wherein said fixed separation distance comprises between 3 and 6 inches.

5. The position indicator of claim 1 further including a level gauge on said circuit board proximate a third aperture, said third aperture providing visual access to said level gauge.

6. The position indicator of claim 5 wherein said first and second laser diodes are arranged on a first end of said enclosure and said level gauge is arranged on a second end of said enclosure opposite said first end.

7. A method for determining a fixed reference distance prior and subsequent to joint replacement surgery comprising the steps of:

providing an enclosure having a pair of first and second laser diodes separated a predetermined distance and a level gauge for maintaining orientation of said laser diodes;

directing a first laser beam originating from said first laser diode onto a first part of a person on one side a joint;

indicating a proximate pre-surgical position on said first part of said person on said one side of said joint;

directing a second laser beam originating from said second laser diode onto a second part of said person on a second side of said joint, opposite said one side of said joint; indicating a distal pre-surgical position on said second part of said person on said second side of said joint;

replacing or repairing said joint;

re-directing said first laser beam onto said proximate pre-surgical position on said first part of said person on said one side of said joint;

re-directing said second laser beam onto said second part of said person on said second side of said joint;

indicating a distal post-surgical position on said second part of said person on said second side of said joint; and comparing said distal post-surgical position to said distal pre-surgical position.

8. The method of claim 7 including the step of aligning said first and second laser diodes with said person.

* * * * *